(12) United States Patent
Sarto et al.

(10) Patent No.: US 10,610,461 B2
(45) Date of Patent: Apr. 7, 2020

(54) PROCESS FOR THE PRODUCTION OF ANTIMICROBIAL DENTAL ADHESIVES INCLUDING GRAPHENE AND RELATIVE PRODUCT THEREOF

(71) Applicant: UNIVERSITA' DEGLI STUDI DI ROMA "LA SAPIENZA", Rome (IT)

(72) Inventors: Maria Sabrina Sarto, Rome (IT); Antonella Polimeni, Rome (IT); Daniela Uccelletti, Rome (IT); Maurizio Bossu', Rome (IT); Agnese Bregnocchi, Rome (IT); Chandrakanth Reddy Chandraiahgari, Rome (IT); Elena Zanni, Rome (IT); Francesca De Angelis, Rome (IT)

(73) Assignee: UNIVERSITA' DEGLI STUDI DI ROMA "LA SAPIENZA", Rome (IT)

( * ) Notice: Subject to any disclaimer, the term of this patent is extended or adjusted under 35 U.S.C. 154(b) by 0 days.

(21) Appl. No.: 16/080,815

(22) PCT Filed: Mar. 1, 2017

(86) PCT No.: PCT/IB2017/051200
§ 371 (c)(1),
(2) Date: Aug. 29, 2018

(87) PCT Pub. No.: WO2017/149474
PCT Pub. Date: Sep. 8, 2017

(65) Prior Publication Data
US 2019/0091109 A1    Mar. 28, 2019

(30) Foreign Application Priority Data

Mar. 2, 2016    (IT) .................. 102016000021868

(51) Int. Cl.
*A61K 6/027*    (2006.01)
*A61K 6/71*    (2020.01)
(Continued)

(52) U.S. Cl.
CPC .................. *A61K 6/71* (2020.01); *A61K 6/17* (2020.01); *A61K 6/30* (2020.01); *A61K 6/76* (2020.01); *A61K 6/831* (2020.01); *A61K 6/884* (2020.01)

(58) Field of Classification Search
CPC ...... A61K 6/0073; A61K 6/08; A61K 6/0088; A61K 6/0023; A61K 6/027; A61K 6/0008
See application file for complete search history.

(56) References Cited

U.S. PATENT DOCUMENTS

2015/0305212 A1*  10/2015  Sarto ..................... H01Q 17/00
                                                              252/511

FOREIGN PATENT DOCUMENTS

CN    104 490 609 A    4/2015
ES    2547476 A1    10/2015
(Continued)

OTHER PUBLICATIONS

He et al., "Killing Dental Pathogens Using Antibacterial Graphene Oxide", ACS applied materials & interfaces, 2015, pp. 5605-5611, vol. 7.
(Continued)

*Primary Examiner* — Jessica M Roswell
(74) *Attorney, Agent, or Firm* — Young & Thompson

(57) ABSTRACT

Disclosed is a dental adhesive including a polymeric adhesive and a nanofiller dispersed in the polymeric adhesive, the nanofiller being constituted by graphene nanostructures which are properly dispersed inside the polymer adhesive and over the surface of the adhesive layer without formation of agglomerates, so that the dental adhesive exhibits signifi-
(Continued)

cant antimicrobial and antibiofilm properties against pathogens of the oral cavity.

22 Claims, 4 Drawing Sheets

(51) Int. Cl.
    A61K 6/17     (2020.01)
    A61K 6/30     (2020.01)
    A61K 6/884    (2020.01)
    A61K 6/76     (2020.01)
    A61K 6/831    (2020.01)

(56) References Cited

FOREIGN PATENT DOCUMENTS

IT   102015000086050      12/2015
WO   2014/140105 A1       9/2014

OTHER PUBLICATIONS

Kulshrestha et al., "A graphene/zinc oxide nanocomposite film protects dental implant surfaces against cariogenic *Streptococcus mutans*", Biofouling: the journal of bioadhesion and biofilm research, 2014, p. 1281-1294, vol. 30.

Hernandez et al., "High-yield production of graphene by liquid-phase exfoliation of graphite", Nature Nanotechnology, 2008, pp. 563-568, vol. 3.

Chang et al., "A highly sensitive ultraviolet sensor based on a facile in situ solution-grown ZnO nanorod/graphene heterostructure", Nanoscale, 2011, pp. 258-264, vol. 3.

Castillo et al., "Preparing graphene derived-polymerizable resins used for dental and medical purpose, involves mixing graphene derivatives with polymerizable resins, where resulting mixture is homogenized to obtain polymerizable resin mixture", Database WPI, Week 201609, XP002760371.

He et al., "Preparing graphene oxide and nano-silicon oxide complex filler-reinforced dental adhesive, comprises blending graphene oxide and 3-aminopropyltriethoxysilane-modified nano-silicon oxide in water and allowing it to stand for precipitation", Database WPI, Week 201550, XP002760324.

Rago et al., "Antimicrobial activity of graphene nanoplatelets against *Streptococcus mutans*", 2015 IEEE 15th International Conference on Nanotechnology, 2015, pp. 9-12.

Santos et al., "Antimicrobial graphene polymer (PVK-GO) nanocomposite films", Chemical Communications, 2011, vol. 47, pp. 8892-8894.

International Search Report and Written Opinion, dated May 9, 2017, from corresponding PCT application No. PCT/IB2017/051200.

Zou et al., "ZnO nanorods on reduced graphene sheets with excellent field emission, gas sensor and photocatalytic properties", Journal of Materials Chemistry A, 2013, pp. 8445-8452, vol. 1.

Dong et al., "Hybrid structure of zinc oxide nanorods and three dimensional graphene foam for supercapacitor and electrochemical sensor applications", RSC Advances, 2012, pp. 4364-4369, vol. 2.

Park et al., "Inorganic nanostructures grown on graphene layers", Nanoscale, 2011, pp. 3522-3533, vol. 3.

* cited by examiner

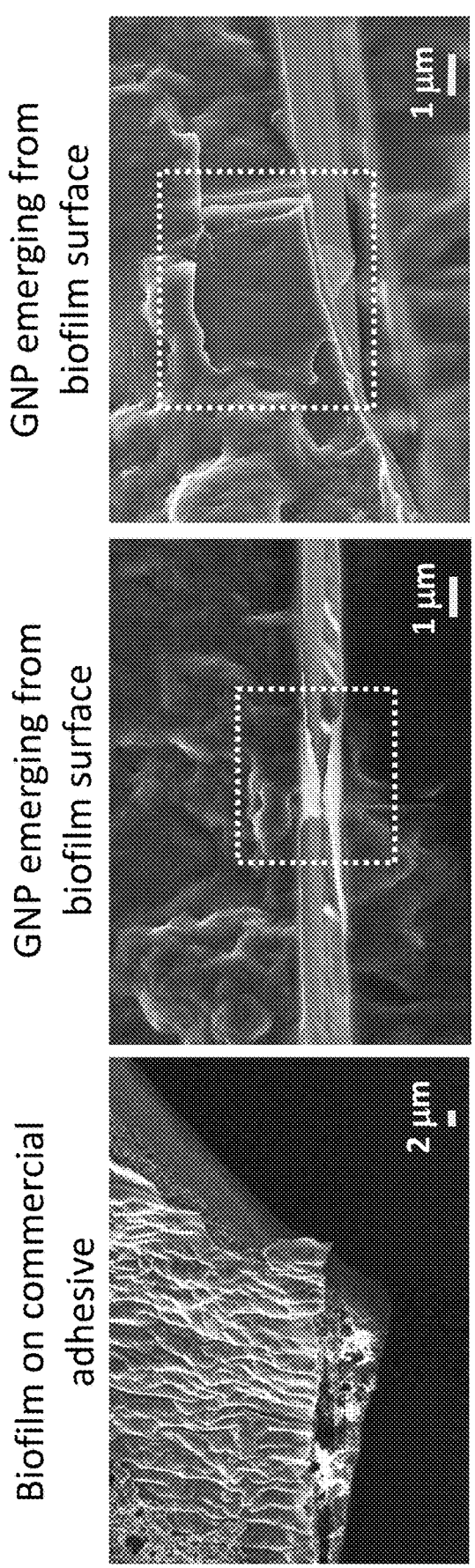
Fig. 5A  Biofilm on commercial adhesive
Fig. 5B  GNP emerging from biofilm surface
Fig. 5C  GNP emerging from biofilm surface

PROCESS FOR THE PRODUCTION OF ANTIMICROBIAL DENTAL ADHESIVES INCLUDING GRAPHENE AND RELATIVE PRODUCT THEREOF

FIELD OF THE INVENTION

The present invention relates to the sector of nanotechnologies and more in particular to formulation and production of polymer-matrix nanocomposites including graphene nanostructures having application as antimicrobial dental adhesive.

In particular, the invention relates to the use of graphene nanoplatelets (GNP) used individually or, decorated with micro/nanorods of metal oxides, doped or not doped, as fillers of polymer adhesive with the purpose of producing new antimicrobial dental adhesives, exerting also an anti-biofilm activity. Nowadays, antimicrobial functions can be obtained through the use of carbon nanotubes (CNT), organometallics, and in general inorganic fillers or metallic nanostructures. However, in these cases the antimicrobial/antibiofilm mechanism is mainly ascribed to the release of ions or to the production of reactive oxygen species (ROS).

In other cases, antimicrobial materials are obtained using antibiotic organic fillers. However, the dispersion of these types of macromolecules in a polymer matrix increases the risk of formation of pockets wherein bacteria proliferate.

The present invention refers to the use of polymer adhesive filled with graphene nanostructured, possibly decorated with nano/microrods of metal oxide, exerting an antimicrobial and antibiofilm activity due to the mechanical interaction between the nanostructured material and the cell wall.

The carbon-based materials are typically black in colour. This reduces their possible use as a filler in dental materials, where aesthetics asks for transparent or white materials. Moreover, curing through photo-polymerization of the composite takes place in situ and requires enough penetration depth of light.

In order to improve both the optical and the antimicrobial properties of the dental adhesive according to the invention, we have developed a process that assure a uniform dispersion of the nanofiller without formation of agglomerates and at the same time it results in a polymer adhesive in which the sharp edges of the nanostructures emerge from the free surface. In addition, we also propose the use of graphene nanoplatelets decorated with nanorods of zinc oxide (ZNG) as nanofiller. Using ZNG, we get excellent antimicrobial properties with a nanofiller weight ratio lower than the one used in case of undecorated graphene nanostructures. Moreover, by controlling the size of the ZnO crystal decorating the surface of the ZNGs, it is possible to modulate the colour and the photoluminescence properties of the new dental adhesive, allowing to improve the cure depth of the resulting light-curing composite. In fact, the ZNG distributed in the polymer matrix are able to absorb and scatter UV radiation, behaving as scattering nodes of UV radiation in the composite material. The resulting composite maintains excellent mechanical properties.

STATE OF ART

The growth of the importance of aesthetics associated to conservative dentistry and of the number of countries involved in international conventions for the protection of the environment and against the use of mercury have led to the need of substituting amalgam, an alloy of mercury at 50% historically used in dental restorations, with alternative materials. The international scientific community has also placed serious questions about possible health consequences of its use as a dental material, so as to be declassified in 2008, from the security level I to level II by the American Food and Drug Administration. Among the most promising materials as a substitute for dental amalgam and for other metallic materials, there are polymer matrix composites. From a clinical point of view, polymer matrix composites are state of the art with regard to the principle of minimum invasiveness and maximum conservation of healthy tissue in the patient. Through the use of polymeric adhesives, these materials can be applied on tooth surface, without the need for removal of healthy tissue. However, polymer matrix composites are subjected to a higher risk of detachment from the dental tissue with respect to amalgam, due to withdrawal or shrinkage during polymerization. Moreover, polymer composite materials for dental applications have in general a shorter life time with respect to amalgam and are used in combination with polymeric adhesives having the function of creating an interface between the tooth and the restoration composite, thus improving adhesion and enabling application in the various portions of the tooth to be restored.

Dental adhesives act as a glue between the hard tooth substance (enamel and dentin), which is hydrophilic and aqueous, and the polymer composite used for restoration, which is rather hydrophobic and water repellent.

Therefore, dental adhesives have adhesion properties both to normal tissues (dentin and enamel) and towards the composites used as fillers in the restoration. In particular, while the adhesion to composites is based on chemical affinity, the adhesion to the dental tissues is of micromechanical nature. In fact, the monomer components of the adhesive diffuse in the microporosity of the tissues and polymerize in situ, sealing them. In practice, dental adhesives have the main function of assuring the dental restoration held. However, one of the major risks that arise during the phase of application of these adhesives is the formation of bacterial biofilms at the interface between adhesive and tooth and/or between the adhesive and resin, which can give rise to de-implantation and detachment phenomena.

One of the greatest possible de-bonding of dental restorations remains the bacterial attack to the material. The proliferation of bacteria in the micro-cavities can lead to breakage and damage of the adhesive interface and cause the detachment of the implant or restoration. It is therefore very important to implement dental adhesives with antimicrobial properties in order to prevent formation of biofilm at the interface between tooth and dental adhesive.

The development of antimicrobial dental adhesives through the use of organic antimicrobials nanofillers, metal or mixtures thereof is known. However, these approaches have limitations, since the organic fillers tend to worsen the mechanical properties of dental materials. In fact, these fillers are subject to shrinkage after the polymerization and phase of care, exactly as the matrix; also they do not have mechanical properties comparable to those of metals and therefore limit the mechanical strength of the composite. As regards the metallic fillers, it is known that typically the toxicological effect of metal nanoparticles is inversely proportional to their size; also it has been demonstrated with studies on animal model ex vivo, that the smaller nanoparticles of silver, and therefore more effective, are toxic if ingested. This represents a serious limitation to their use in oral devices.

Finally, it has been repeatedly reported that the use of antimicrobial agents, antibiotics and bactericides containing chemical, might affect the balance between the bacterial flora of the mouth and digestive system cable.

Among the most promising antimicrobial fillers, we have to mention metal oxides. These materials, due to their typically white coloration are particularly used in the dental sector. However, in order to achieve an antimicrobial effect, the percentage in minimum weight of metal oxides for inclusion in polymer matrices are typically high—from several tens up to a few percentage units by weight—such as to make the material highly viscous. This makes them, to date, interest in the production of composite restorative, but not usable in low-viscosity adhesives.

In the prior art Spanish patent application ES2547476 discloses a method for the production of polymerisable resins with graphene derivatives, comprising the following steps of: a) mixing the graphene derivative with the solid component of the polymerisable resin and homogenising the mixture; b) polymerising the compound obtained in step (a), without the addition of solvents; c) polymerising in water at controlled pressure and temperature for 30 minutes. The invention also relates to the polymerisable resin obtained using the method of the invention and to the use of same for medical and dental purposes, as heat-stable coatings, heat-stable adhesives and sealants in construction and civil engineering, as heat-stable adhesives in aerospace and aeronautical engineering, and as heat-stable adhesives and sealants in automotive engineering. The disclosed process which is characterized by the fact not to include the addition of a solvent, meets the required mechanical properties, but has no antimicrobial activity.

Chinese patent application CN 104 490 609 discloses a method for the preparation of a graphene oxide and nanosized silica composite filler reinforced binder for dentistry. The method comprises the following steps: preparing a graphene oxide and nanosized silica composite; performing surface modification for graphene oxide and nanosized silica; compositing graphene oxide and nanosized silica with the binder to obtain the binder for dentistry. The obtained binder for dentistry is relatively high in binding strength; a graphene oxide and nanosized silica composite filler can be dispersed well in the binder; in addition, the modified composite filler is amphiphilic and can permeate dentin well while being applied to the binder for dentistry, so that the binding strength with the dentin is improved. However, the disclosed process is based on numerous complex steps including:
a. Blending graphene-oxide and modified nano-silicon oxide in water, stirring to mix;
b. allowing it to stand for precipitation, removing surnatant, freezing-dry the precipitate thus obtaining composite graphene-oxide and nano-silicon oxide powders;
c. Dissolving the composite powders in water and mixing with other components including toluene;
d. Mixing with adhesive and numerous other components, but, moreover, makes use of toxic solvent, such as toluene, which obviously is not recommended considering the application in the dentistry field. Jianliang He et al. Killing Dental Pathogens Using Antibacterial Graphene. Oxide ACS Appl. Mater. Interfaces, 2015, 7: 5605-5611, teaches a derivative of grapheme, graphene oxide (GO), as a promising antimicrobial nanomaterial. In this study, Authors focused on the antimicrobial property of GO against dental pathogens; by MTT test, colony forming units (CFU) counting, growth curve observation, live/dead fluorescent staining, and confocal laser scanning microscopy (CLSM), found GO nanosheets were highly effective in inhibiting the growth of dental pathogens.

Transmission electron microscopy (TEM) images revealed that the cell wall and membrane of bacteria lost their integrity and the intracellular contents leaked out after they were treated by GO. Therefore, GO nanosheets are suggested to be an effective antibacterial material against dental pathogens and potentially applicable in dental care and therapy. However, it is worthy to point out that graphene oxide application induces antimicrobial activity by producing ROS, hence this technical solution has an intrinsic citotoxicity, moreover the publication does not teach how to maintain the ROS unrelated antimicrobial properties of grapheme nanostructures in order to produce a dental adhesive by a properly homogeneous dispersion inside a polymer matrix.

Kulshrestha S. et al. A graphene/zinc oxide nanocomposite film protects dental implant surfaces against cariogenic *Streptococcus mutans*. Biofouling The Journal of Bioadhesion and Biofilm Research. 2014. 30: 1281-94, explored the potential of graphene/zinc oxide nanocomposite (GZNC) against the cariogenic properties of *Streptococcus mutans* and the antibiofilm behaviour of artificial acrylic teeth surfaces coated with GZNC. Acrylic teeth are a good choice for implants as they are low cost, have low density and can resist fracture. Microscopic studies and antibiofilm assays have shown a significant reduction in cariogenic biofilm in the presence of dental implants GZNC coating. According to Kulshrestha S. et al. the production of the nanocomposites takes place at very high temperatures (120° C.) directly on the synthetic tooth surface to form a nanocomposite film protecting dental implant surfaces against cariogenic *Streptococcus mutans* and are not involved in the formation of a dental adhesive polymeric matrix wherein nanocomposites are uniformly dispersed. The international patent application WO 2014/140105 relates to dental cement or filler material composition comprising graphene and/or deuterium oxide or deuterium and their uses in direct or indirect dental restoration and/or prevention. According to this invention graphene platelets are obtained by liquid-phase exfoliation of graphite in organic solution by a sonication cycle (Hernandez Y. et al., High-yield production of graphene by liquid phase exfoliation of graphite. Nature Nanotechnol. 3, 563-568, 2008). Pulsed mode sonication (2 s pulses with 1 s interval) of the graphite solution at highest power (200 W) for 20 min. in a thermostated water bath (40° C.) is performed. Unfortunately, the procedure uses N-methylpyrrolidone as solvent, which is highly toxic. Therefore, the process of incorporation of graphene nanoparticles known in the prior art cannot yet be considered as optimized, the proposed methods are often complex, requiring the use of organic solvents or water, and especially do not guarantee an adequate dispersion of nanoparticles in the polymer matrix.

The US patent application US 2015/305212 discloses a process to produce nanocomposites filled with graphene nanoplatelets, having improved electromagnetic properties, to be used as radar absorbing material, The disclosed process to produce such thermosetting or thermoplastic polymer based composite filled with graphene nanoplatelets includes several steps which are aimed at the optimization of the electromagnetic properties of the composite, and in particular it is based on the exfoliation of expanded graphite in an acetone/DMF mixture.

There is therefore a need for a method of incorporating nanoparticles of graphene in polymer matrices for the production of dental adhesives that have antimicrobial properties which overcome all the drawbacks described in the prior art.

SUMMARY OF THE INVENTION

A first object of the present invention is to provide a process for producing dental adhesives that exhibit strong antimicrobial and antibiofilm properties against bacteria that typically inhabit the oral cavity, such as *S. mutans*, having appropriate mechanical characteristics and adhesion to the tooth and ensuring appropriate depth of cure.

Another object of the present invention is to provide dental adhesives, obtainable by said process, that exhibit strong antimicrobial and antibiofilm properties against bacteria that typically inhabit the oral cavity, such as *S. mutans*.

Another object of the invention is to provide dental adhesives, obtainable by said process, with antimicrobial properties which ensure appropriate mechanical characteristics and adhesion to the tooth. Another object of the present invention is to provide dental adhesives, obtainable by said process, ensuring an appropriate depth of cure.

The present invention achieves these and other objects that will be clear in light of the present description, by providing a dental adhesive which, in accordance with claim 1, comprises a polymeric adhesive and a nanofiller dispersed in the polymeric matrix, the nanofiller being constituted by graphene nanostructures which are properly dispersed inside the polymer adhesive without formation of agglomerates and trapped with the polymer chains so that their sharp edges are exposed over the adhesive surface, originating a mechanic antimicrobial action.

Therefore, the present invention provides dental adhesives loaded with graphene or graphene-based nanostructures, which act as nano-fillers. Due to a suitable selection of the antimicrobial filler and of the mixing and curing process, the dental adhesives of the invention exhibit pronounced antimicrobial properties while maintaining unaltered the mechanical properties and initial adhesion.

For example, the mechanical and adhesion characteristics are kept unchanged with respect to a commercial adhesive with no addition of a nanofiller or a nanomaterial. This allows associating the curative purpose of dentistry an approach to prevention of the onset of microbial infections.

In particular, the present invention provides antimicrobial nanocomposites adhesives for dental applications, based on the use of nanostructures of graphene such as graphite/graphene nanoplatelets (GNP), or nanoplatelets of reduced graphene oxide, or of multilayer graphene flakes, dispersed in a polymeric adhesive in order to obtain a nanocomposite with antimicrobial properties. Possibly the nanostructures of graphene are decorated, or functionalized with ZnO nanorods.

According to the invention, the typical graphene based dental adhesive features are due to the specific optimized production process by which the dental adhesive is obtainable, enabling to induce antimicrobial properties towards at least one bacteria specie of the oral cavity, in particular towards the gram-positive bacteria specie responsible for initiation of the dental plaque, pivotal in caries formation and development also in cured teeth, *S. mutans*.

Although the present invention is described referring to a dental adhesive to dentin or enamel, it is applicable in more general framework of the polymeric materials in the field of orthodontics.

The antimicrobial properties of the adhesive according to the invention were verified experimentally by viability tests and inhibition of biofilm formation using, as an example and not as limitation, the graphene nanoplatelets (GNP) produced from commercial GIC (Graphite intercalation compound) as nanofiller.

Advantageously, the antimicrobial dental adhesives of the invention diminish the occurrence of caries and the formation of biofilms, acting at the interface tooth-restoration and increasing the life time of the restoration, while maintaining excellent mechanical characteristics and adhesion on the tooth, the latter being comparable to those of existing commercial adhesives.

Advantageously, the graphene materials such as graphene nanoplatelets (GNPs), or nanoplatelets of graphene oxide or reduced graphene oxide or multilayer graphene flakes or a combination thereof, used as nanofiller in the adhesive of the invention, if properly dispersed according to the process disclosed in the present invention, enable the adhesive to exhibit a strong antimicrobial capacity. This permits to overcome the limitations related to shrinkage and toxicity of existing solutions, and also to obtain a marked antibacterial activity already at low concentrations (for example 0.5 mg/mL of *S. mutans*), without inducing ROS (Reactive Oxygen Species) production in the treated cells.

The antimicrobial function of the graphene-based adhesive in the present invention is mainly due to the direct interaction between the nanostructured rough surface of the nanomaterial and the bacteria cell wall, such as *S. mutans*. In fact, favorably, the graphene based nanostructures, if properly dispersed in the polymer adhesive, are partially exposed over the adhesive free-surface with their sharp geometry and consequently they are able to mechanically damage the cell wall by direct contact, thus inhibiting biofilm formation.

In particular, the developed antimicrobial adhesive takes advantage of a killing mechanism based on the mechanical interaction between nanostructures emerging from the adhesive surface and the bacteria cell walls, and of the biofilm anti-adhesion effect typical of graphene. The technical solution proposed in this invention consists in developing a GNP-filled polymer adhesive that enables to combine the anti-adhesion properties of graphene towards bacteria biofilm, with the antimicrobial activity of graphene-based nanoplatelets or of decorated GNPs, without producing a surplus of reactive oxygen species (ROS), which are correlated to higher cytotoxicity.

By contrast, the antimicrobial effect of additive products with metal nano-particles according to the state of art, is tied to the release of ions or the production of reactive oxygen species (ROS).

According to a particularly preferred embodiment of the invention, the graphene based nanostructures are functionalized, or decorated, with a metal oxide, in particular with zinc oxide micro- and/or nanostructures. Advantageously, the presence of ZnO nanorods grown on the surface of the nanostructures, for example of the graphene nanoplatelets, has a dual function: on the one hand it contributes to enhance the antimicrobial effect associated with direct damage to the bacteria cell wall; on the other hand it improves the optical characteristics of the undecorated graphene nanostructures that have a typically high absorption in the visible light spectrum, which can limit the effectiveness of the photopolymerization techniques during the application on the tooth step. In fact, it has been shown that the ZnO nanorods, following ultrasound treatment in a suitable solvent (such as ethanol), have fluorescence characteristics at short wave lengths of the visible (typically in the blue), acting therefore within the polymer as scattering points for the ultraviolet radiation (typically used in the processes of photopolymerization of dental adhesives). Thus, this results in an increased cure-depth of the adhesives loaded with graphene nanostructures, such as graphene nanoplatelets decorated with ZnO nanorods (ZNG) and in optimal mechanical properties and adhesion of the final product applied on the tooth.

According to the first object of the invention, the process for the production of the dental antimicrobial adhesive including a polymer adapted to form the polymer adhesive, a nanofiller, a solvent, comprises the steps of:

a. Preparation of a suspension of nano-filler in aqueous solution of ethanol having concentration between 0.1 mg/mL and 15 mg/mL, depending on filler type and amount.

b. Addition of the polymer adhesive to the nano-filler suspension to obtain the antimicrobial dental adhesive having a specific concentration of nano-filler between 0.05% in weight and 0.5% in weight of the polymer matrix, preferably the concentration of nano-filler is 0.2% in weight of the polymer matrix.

c. Controlled slow-rate evaporation of the solvent in excess at constant temperature, comprised between 15° C. and 40° C., and room pressure through mechanical stirring at velocity of 50-500 rpm, for a time comprised between 0.5 h and 24 h. The evaporation process is stopped when the mixture has a total over weight with respect to the original polymer content comprised between the 105% and the 150%, and preferably the 120%, so that the resulting mixture is characterized by a Newtonian rheological behavior, with measured viscosities comprised between 0.01 and 0.1 Pa s, enabling a uniform application of the antimicrobial dental adhesive in the dental cavities;

d. Air flushing of the free-surface of the antimicrobial dental adhesive with a controlled air-flux pressure comprised between 0.03 and 0.9 bar, preferably 0.2 bar.

e. UV/vis polymerization for time comprised between 5 and 30 s at an intensity greater than 500 mW/cm$^2$, preferably greater than 800 mW/cm$^2$.

According to the invention, once the suspension of nano-filler and solvent is prepared in step a. of the process, in step b. an amount of polymer matrix is added to this suspension such that the resulting composite contains an amount of nanofiller comprised between 0.05% and 0.5% of the weight of the added polymer matrix.

In particularly preferred embodiments of the invention the concentration of the nano-filler in aqueous solution of ethanol has concentration of 0.5 mg/mL when a GNP produced nanofiller via exfoliation or expanded graphite through ultrasonication are used, or the nano-filler in aqueous solution of ethanol has concentration of 5 mg/mL when ZNG dispersed nanofiller via bath sonication is used.

The technical features of the air flushing step (d) in the process according to the invention relating the air flux pressure enable to obtain a film with thickness comprised between 0.5 and 25 micron, preferably 15 micron, and avoid filler agglomeration and material losses during spreading, and create a controlled roughness of adhesive free-surface with nanostructures emerging from the polymer adhesive.

SHORT DESCRIPTION OF FIGURES

Further characteristics and advantages of the invention will appear more evident in light of the detailed description of the preferred, but not exclusive, embodiments of the invention illustrated in the attached figures. Examples of processes to obtain a dental adhesive according to the invention are also described.

FIG. 1A illustrates a SEM micrograph of GNP used in the invention;

The FIG. 1B illustrates a SEM micrograph of GNP decorated with zinc oxide nanorods used in the invention;

FIG. 2 illustrates the evaluation of the adherence ability of S. mutans to the adhesives of the invention (columns 2 and 3 of the figure) and to the commercial adhesive devoid of nanostructures, used as a control (column 1 of the figure);

FIG. 5A illustrates a SEM micrograph of the biofilm formed by S. mutans in the presence of the commercial adhesive;

FIG. 5B illustrates a SEM micrograph of the biofilm formed by S. mutans in the presence of an adhesive of the invention;

FIG. 5C illustrates a magnification of a graphene nanoplatelet that alters the structure of the biofilm formed by S. mutans.

DETAILED DESCRIPTION OF A PREFERRED FORM OF REALIZATION

Figures 1A, 1B:
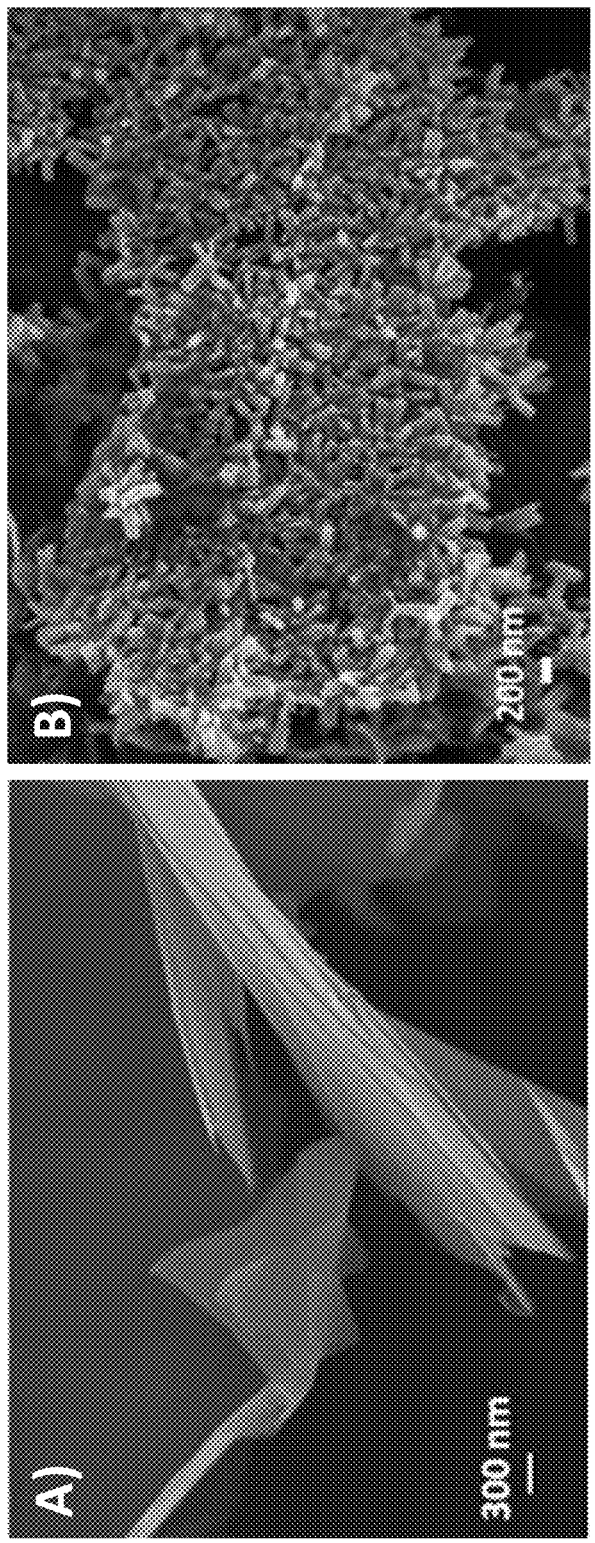

According to a particularly preferred embodiment of the invention, an antimicrobial dental adhesive comprising a polymer adhesive and a nanofiller uniformly dispersed inside the adhesive is provided. The nanofiller is made of graphene nanostructures, and in particular it consists of graphene nanoplatelets (GNP), which are produced through liquid-phase exfoliation of expanded graphite. In this preferred embodiment, the process for the production of antimicrobial dental adhesives is carried out as above described with specific conditions for the initial two steps as follows:

a. Preparation of a suspension of expanded graphite in aqueous solution of ethanol at 99% having expanded graphite concentration (C measured in mg/mL) between 0.1 mg/mL and 1 mg/mL, preferably the concentration is C=0.5 mg/mL. The exfoliation of the expanded graphite is carried out by sonication with a power output per unit of surface transferred from the tip of the sonotrode to the liquid between 20% and 100% of the maximum value that the sonotrode can provide, preferably the 70% of the maximum value that the sonotrode can provide, with a pulsed cycle with 1 sec on-phase and 1 second off-phase, for a total time of activity between 10 and 60 minutes, typically 20 minutes, at a controlled temperature comprised between 10 and 20° C., preferably at the temperature of 15° C. The resulting colloidal suspension is a suspension of graphene nanoplatelets (GNP) in ethanol at 99%.

b. Addition of an amount of polymer adhesive (P_polymer measured in g), such as any type among those commercially available, to a volume of the aforesaid colloidal suspension of GNP in ethanol at 99% (V_GNP_suspension measured in mL) according to the following formula:

$$V\_GNP\_suspension = 10 \times W\_GNP\ \% \times P\_polymer/C$$

Wherein W_GNP (%) is the GNP weight in percent over the weight of polymer adhesive, typically comprised between 0.05% in weight and 0.5% in weight, preferably 0.2% in weight, and C is the concentration of expanded graphite in ethanol as specified in a).

In other words, at first expanded graphite is dispersed in a suitable amount of ethanol in order to proceed to exfoliation of the expanded graphite and produce a suspension of graphene nanoplatelets. In this phase it is important to set the concentration of expanded graphite with respect to the amount of ethanol. In fact the features of nanoplatelets that will be produced by the process of exfoliation depend on this concentration. Out of the suggested values range nanostructures with the desired characteristics are not obtained. Such concentration of expanded graphite in ethanol is chosen independently from the concentration of nanostructures respect to the polymer which then characterizes the final adhesive.

Alternatively, according to another embodiment, the nanofiller is made either of reduced graphene oxide nanoplatelets, or of multi-layered graphene flakes. These nanostructures have typical lateral dimensions comprised between 300 nm e 10 µm, and thickness comprised between 1 nm e 25 nm. Preferably, they have lateral dimensions between 0.5 µm e 3 µm and thickness between 5 nm and 10 nm. In particular, GNPs are composed by a number of staked graphene planes comprised between 1 and 70, and thickness comprised between 0.335 nm and 25 nm.

Moreover, the nanostructures are dispersed in a weight concentration with respect to the total weight of the polymer adhesive, comprised between 0.05% in weight and 0.5% in weight, preferably the 0.2% in weight. FIG. 1A shows a scanning electron microscopy (SEM) micrograph of GNPs used in the invention.

In another embodiment, the invention provides an antimicrobial dental adhesive comprising a polymer adhesive and a nanofiller uniformly dispersed inside the adhesive, wherein the nanofiller is made of graphene nanoplatelets or graphene-based nanoplatelets decorated with ZnO nano or micro rods (ZNG), eventually doped with metals, like for instance magnesium or lithium.

Alternatively, according to one of the different realization of the first embodiment, the nanofiller is made either of reduced graphene oxide nanoplatelets, or of multi-layered graphene flakes, which are decorated with ZnO nano or micro rods, eventually doped with metals.

The ZnO nanostructures are preferably nanorods having diameter comprised between 20 nm and 500 nm and length comprised between 200 nm and 3 µm. Moreover, ZNGs are dispersed in a weight concentration with respect to the total weight of the polymer adhesive, comprised between 0.05% in weight and 2% in weight, preferably the 0.2% in weight.

FIG. 1B shows a scanning electron microscopy (SEM) micrograph of ZNGs used according to the invention. Preferably, for the production of a dental adhesive according to the invention, it is necessary to have a polymer adhesive, a nanofiller, a solvent. In this preferred embodiment, the initial two steps of the process are specified as follows:
  a. Preparation of a suspension of ZNGs in aqueous solution of ethanol at 99% having ZNG concentration between 0.1 mg/mL and 15 mg/mL, corresponding to a filler weight ratio comprised respectively between 0.05% in weight and 0.5% in weight of the total amount of polymer adhesive, and dispersion of the ZNGs through ultrasonic bath for a duration comprised between 20 s and 10 min, typically 5 min;
  b. Addition of the polymer adhesive to the suspension to obtain the antimicrobial dental adhesive, in a specific ratio corresponding to a filler weight concentration over the polymer adhesive comprised between 0.05% in weight and 0.5% in weight, preferably 0.2% in weight;

Alternatively, ZNGs, GNPs, graphene flakes, multilayer graphene flakes, reduce-graphene oxide nanoplatelets, graphite nanoplates or a combination of them can be used.

The solvent used in the step of nanofiller exfoliation and/or dispersion is chosen in such a way to be compatible with the starting polymer adhesive, i.e. that it does not degrade the polymer adhesive and at the same time maximizes the solubility of the nanofiller, so as to obtain an excellent and uniform dispersion. In addition to ethanol at 99% in water, also other organic or inorganic solvents may be used, such as water, ethanol, acetone, glutaraldehyde, their mixtures in any ratio sufficient and necessary to maintain suspension of the nanofiller, and to ensure specific chemical functions depending on the type of polymer adhesive used.

In any case, the suspension of graphene-based nanofiller is added with the polymer adhesive in a suitable percentage by weight so that the total amount of nanofiller is comprised typically between 0.05% in weight and 0.5% in weight of the total polymer adhesive weight.

The mixture is subjected to mechanical stirring in order to maintain high dispersion of the nanofiller avoiding the formation of agglomerations during the slow evaporation of the solvent. The procedure has a variable duration of between 2 minutes and 24 h, depending on the concentration of ethanol in water and the concentration of the initial suspension of nanofiller in solution. For example, using ethanol 99% in water, evaporation has a duration between 3 and 9 hours, preferably about 6 hours. The temperature of the mixture is kept constant during the stirring typically to a value dependent from the characteristics of the polymer and the solvent used. The magnetic stirring is preferably carried out using a central support of cylindrical shape as described in the patent US2015/0305212, with the scope of imparting to the magnetic anchor a motion of revolution, as well as rotation around its axis, thus preventing the formation of agglomerations of nanofillers in the mixture.

At the end of the evaporation phase, the mixture is casted in molds according to the final application, or applied directly to a tooth according to standard clinical protocols. The subsequent phase of air-flushing plays a fundamental role in order to maintain a uniform dispersion of the nanofiller in the polymer adhesive and to obtain a rough surface of the adhesive, characterized by the sharp edges of the nanostructures that emerge from the polymer adhesive, thus exerting the antimicrobial/antibiofilm action.

The subsequent photo-polymerization occurs in air, as described above.

In a preferred embodiment of the invention the commercial polymer adhesive used to be added to the suspension to achieve it can be a product including bisphenol A glycidyl methacrylate (Bis-GMA), hydroxyethyl methacrylate (HEMA), possibly containing solvents, such as water, acetone, optionally containing further nanofillers, for example silicate.

In a preferred embodiment of the invention the GNP decoration with ZnO nanostructures can be obtained, without limitation to this, using conventional techniques, as described in Haixin Chang, et al., Nanoscale, 2011, 3, 258, oppure in Rujia Zou, et al., J. Mater. Chem. A; 2013, or in Xiaochen Dong, et al., RSC Advances, 2012, 2, 4364-4369, or in Won Il Park, et al., Nanoscale, 2011, or according to the procedure described in Haixin Chang, et al., Nanoscale, 2011, 3, 258, or in Rujia Zou, et al., J. Mater. Chem. A; 2013, or in Xiaochen Dong, et al., RSC Advances, 2012, 2, 4364-4369, or in Won Il Park, et al., Nanoscale, 2011, 3, 3522 or according to the procedure described in the Italian patent application no. 102015000086050 of 21 Dec. 2015.

In the latter, the decoration of the GNP takes place by hydrothermal growth in static conditions or under mechanical agitation, or by sonication with an ultrasonic probe at room temperature of an aqueous suspension of GNP and salts containing Zinc nitrate hexahydrate. In all three cases, preferably, but not exclusively, the production procedure of ZNGs with control of the morphology comprises the following steps:

Step 1: production of an aqueous suspension of graphene nanoplatelets (GNP);
Step 2: deposition of seed layer of unsupported GNP in aqueous suspension;
Step 3: growth of ZnO nanorods and/or microrods of ZnO on unsupported GNPs in aqueous suspension.

After providing an illustrative description of some adhesives according to the invention, and some processes to achieve them, in the following there are described the results of the functional tests carried out with such adhesives.

EXAMPLE 1—Characterization Test of the Mechanical and Adhesion Properties

As previously described, dental adhesives with antimicrobial properties according to the invention are products with concentrations of GNPs typically between 0.05% and 0.5% and retain the mechanical properties and adhesion to dentin of commercial adhesives. In this test, a dental adhesive containing GNPs at a concentration of 0.2% in weight was used.

The adhesives produced were subjected to microtensile test according to the following protocol:

1) In the case of adhesion tests, the product material is applied on the tooth previously prepared by means of lapping step (600, 2500, 4000) and acid etching through a chelator of calcium, by way of example and not of limitation, orthophosphoric acid at 37%, and rinsed.
2) The resulting tooth is used as substrate for the application of the adhesive, which is finally treated with a jet of clean air at pressures typically between 0.03 and 0.9 MPa in order to allow the quick evaporation of residual solvents and photo-polymerization.
3) The adhesive is covered with a layer of composite for dental restorations, by way of example and not of limitation, the 3M Filtek™ 2250, which is cured according to the manufacturer's instructions.
4) The tooth and the dental restoration are cut according to the reference standards and tested with a universal testing machine INSTRON suitably equipped for microtensile testing.

The values of the force of adhesion between adhesive and dental tissue are completely in line, or are comparable, with the data obtained for the untreated commercial adhesives, and are typically comprised between 30 MPa and 34 MPa.

EXAMPLE 2—Test on Adhesive Penetration Capacity

Tests analysing adhesive penetration were conducted based on the following procedure:

1) The material is placed in metal molds of which the base and the side surfaces are previously optically shielded.
2) The sample thus prepared is light cured from the upper surface for times not lower than the 10 s (for example, but not limiting, 20 s).
3) The portion of polymerized adhesive is extracted and the thickness measured with a digital micrometer.

The minimum penetration capacity for the adhesives loaded with GNP at 0.2% in weight was 2 mm, while for the adhesives loaded with ZNGs at 0.2% in weight was always greater than about 4.4 mm.

The increase of the penetration of the adhesive loaded with ZNGs is attributable to the action of scattering of the ultraviolet light exerted by the nanostructures of ZnO, that once treated in ethanol show fluorescence in this band of visible.

EXAMPLE 3—Antimicrobial Test

The experiments for the evaluation of the antimicrobial properties were carried out by analyzing the capacity of adhesion of bacterial cells to the various types of adhesive, using the *S. mutans* collection strain ATCC 25175. The bottom of the wells of a microplate were coated with the composite, ie, with the adhesive and $1\times10^6$ bacterial cells, from a fresh culture, were added and incubated in BHI for 24 hours. The cell survival was evaluated through the method of colony forming units (CFU). The control used was the composite devoid of GNP and reported as 100% of cell survival.

Likewise the same test was carried out in the case of the composite containing GNP decorated with metal oxides, in the specific case are reported the effects with Zinc oxide.

Figure 2:
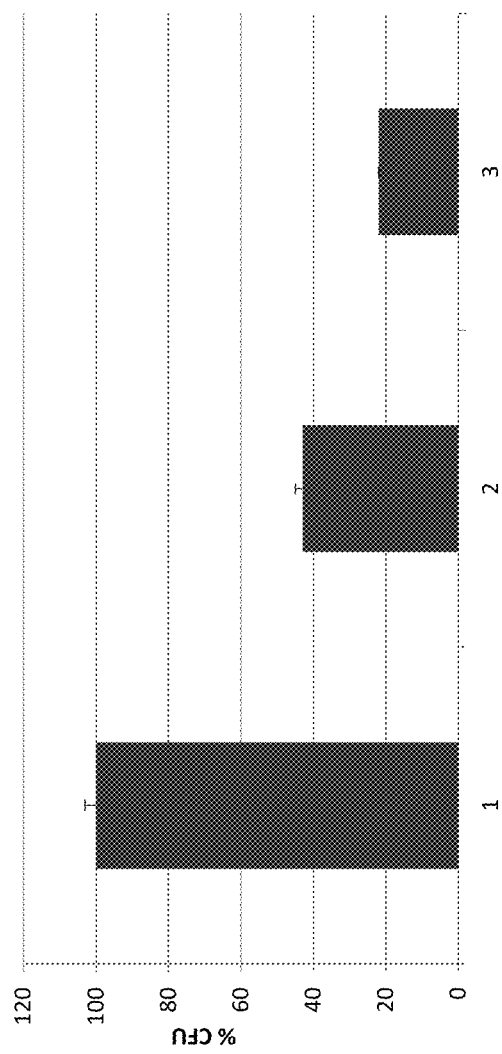

As can be seen from FIG. 2, the composite with GNP decorated is more efficient. In particular, FIG. 2 shows the results of the experiments carried out: as is in column 1 with a commercial adhesive; with adhesive loaded with GNP 0.2% in weight in column 2; with adhesive loaded with GNP decorated with ZnO nanorods 0.2% in weight in column 3.

Figure 3C:
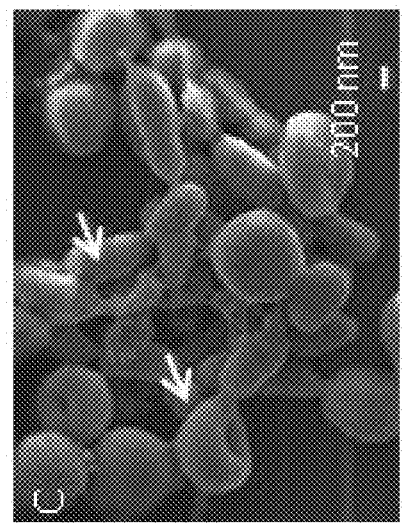
FIG. 3C illustrates a SEM micrograph of S. mutans treated with another adhesive of the invention.
Figure 3B:
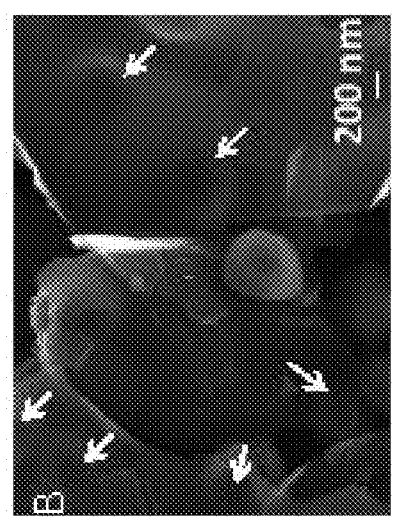
FIG. 3B illustrates a SEM micrograph of S. mutans treated with an adhesive of the invention.
Figure 3A:
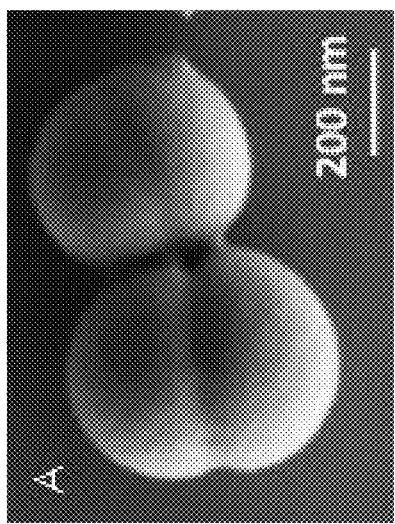
FIG. 3A illustrates a SEM micrograph of untreated S. mutans cells.

The results obtained are in agreement with the mechanical effect of damage of the bacterial cell wall by the graphene based nanostructures, as observed by a scanning electron microscope analysis (SEM). In fact, as shown in FIG. 3, when *S. mutans* is treated in suspension for 24 hours with the GNP or GNP decorated with, SEM analysis shows a massive deterioration of the cells. In particular, FIG. 3 shows SEM photomicrographs of *S. mutans* untreated (3A), after treatment for 24 hours with GNP (3B) or with GNP decorated with ZnO nanorods. In FIG. 3B the arrows indicate the cells, trapped in pieces of GNP. In FIG. 3C the arrows indicate the many cells completely destroyed by the treatment.

Because the biofilm is critical in the formation of caries, it was then analyzed the ability of the adhesives loaded with the two types of filler (ie GNP and GNP decorated with ZnO nanorods) to alter the formation of biofilm directly on cured teeth.

The evaluation of the biofilm on the composite distributed on the teeth with a spatula was carried out by the Crystal Violet method. As seen from FIG. 4A a reduction of staining was obtained compared to the control composite with both, the adhesive containing as nanofiller the GNP at 0.2% in weight and that containing ZNGs 0.2% in weight as filler. The quantitative evaluation of the Crystal Violet showed in the case of GNP filler, as an example and not as limitation, a net reduction of the formation of biofilm by bacterial cells compared to control adhesive. In particular, FIG. 4 illustrates the evaluation of the biofilm formed by *S. mutans* on the treated teeth. The FIG. 4A illustrates a qualitative assessment through Crystal Violet on teeth treated with control adhesive (NT), with the GNP-based fillers 0.2% in weight (GNP) and with the GNP decorated with ZnO 0, 2% in weight (GNP-ZnO) based filler.

Figure 4B:
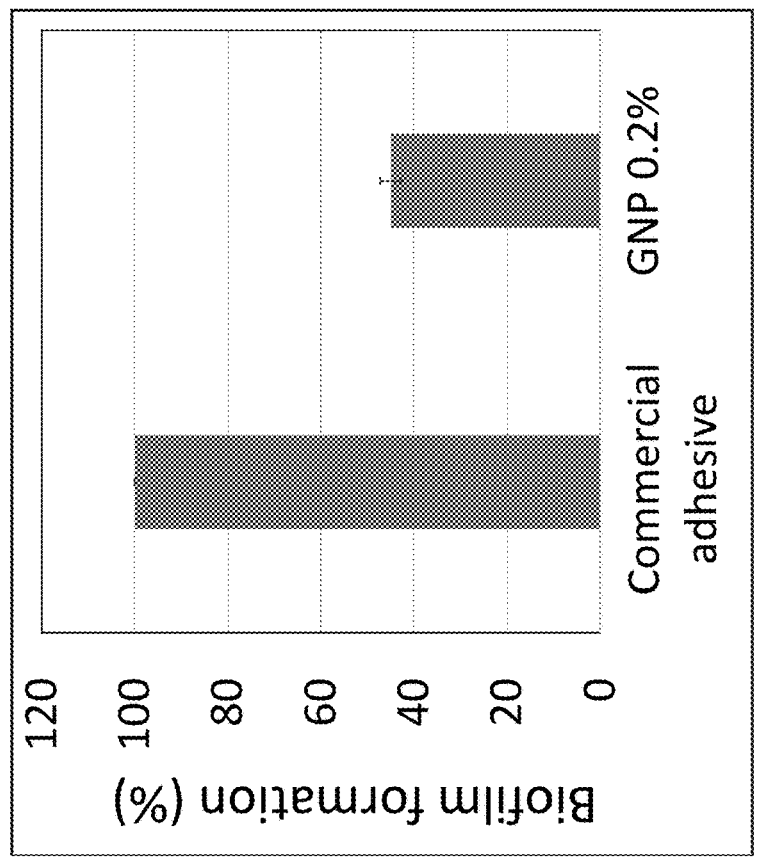
FIG. 4B illustrates a quantitative assessment of biofilm formed by S. mutans.
Figure 4A:
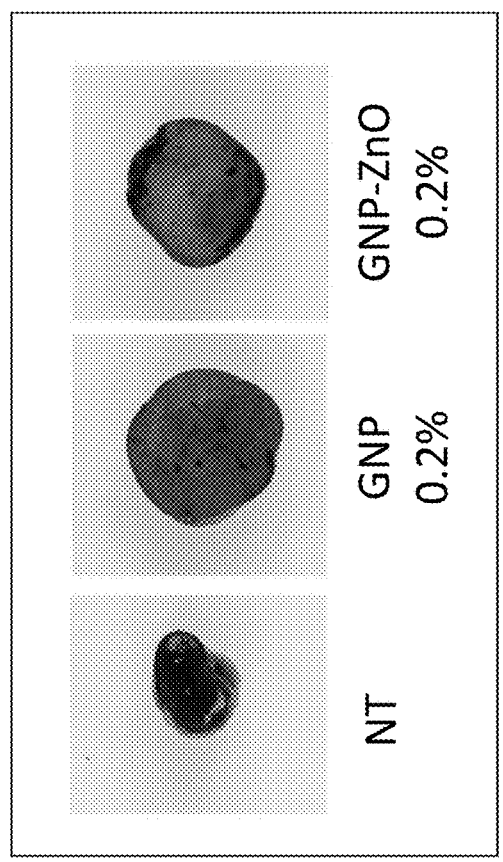
FIG. 4A illustrates a qualitative assessment of the biofilm formed by S. mutans.

The FIG. 4B illustrates a quantitative analysis performed with the same dye, comparing the teeth treated with control adhesive and with the one containing the GNP 0.2% in weight as filler.

The SEM analysis of the samples showed that the structure of the biofilm growing on the surface of the new adhesive is morphologically altered compared to that observed on the surface of the commercial adhesive. As an example, in FIG. 5 is shown what observed in samples made with adhesive loaded with GNP undecorated. The photomicrographs performed on the sample used as control in the antimicrobial efficacy tests show that the polymer matrix produced by the bacteria during the formation of the biofilm is clearly observable with the preserved bacterial structures. On the contrary, in the case of adhesive loaded with GNP the shape of bacteria lying down on the biofilm matrix it is no longer recognizable in a defined way, because of mechanical interaction between GNP and bacteria. In particular, FIG. 5 shows SEM photomicrographs of biofilm formed by *S. mutans* in the presence of the commercial adhesive (FIG. 5A) or the adhesive that contains the graphene-based fillers (GNP 0.2% in weight) (FIG. 5B). In FIG. 5C is shown the magnification of a sheet of GNP that alters the structure of the biofilm.

The invention claimed is:

1. A process for producing dental adhesives having strong antimicrobial and antibiofilm properties against bacteria that typically inhabit the oral cavity having appropriate mechanical characteristics and adhesion to the tooth and ensuring appropriate depth of cure, the process comprising:
   a) preparation of a nano-filler suspension, made of graphene or graphene-based nanostructures, graphene nanoplatelets (GNP), nanoplatelets of reduced graphene oxide, multilayer graphene flakes or a combination thereof, in aqueous solution of ethanol having concentration between 0.1 mg/mL and 15 mg/mL, depending on filler type and amount;
   b) addition of a polymer adhesive to the nano-filler suspension to obtain an antimicrobial dental adhesive having a specific concentration of nano-filler between 0.05% in weight and 0.5% in weight of the polymer matrix;
   c) controlled slow-rate evaporation of the solvent in excess at constant temperature, comprised between 15° C. and 40° C., and room pressure through mechanical stirring at velocity of 50-500 rpm, for a time comprised between 0.5 h and 24 h when the mixture has a total over weight with respect to the original polymer content comprised between the 105% and the 150%;
   d) air flushing of a free-surface of the antimicrobial dental adhesive with a controlled air-flux pressure comprised between 0.03 and 0.9 bar;
   e) UV/vis polymerization for time comprised between 5 and 30 s at an intensity greater than 500 mW/cm$^2$.

2. The process according to claim 1 wherein in the antimicrobial dental adhesive the concentration of nano-filler is 0.2% in weight of the polymer matrix.

3. The process according to claim 1 wherein the controlled slow-rate evaporation of the solvent in excess is stopped when the mixture has a total over weight with respect to the original polymer content of 120%.

4. The process according to claim 1 wherein the air-flux pressure is 0.2 bar.

5. The process according to claim 1 wherein the intensity is greater of 800 mW/cm$_2$.

6. The process according to claim 1 wherein the graphene, or the graphene-based nanostructures, are decorated, or functionalized with metal oxide.

7. The process according to claim 6 wherein the graphene, or the graphene-based nanostructures are decorated, or functionalized with zinc oxide micro-and/or nanostructures, or nanorods.

8. The process according to claim 1 wherein the polymer adhesive to be added to the nano-filler suspension to obtain the antimicrobial dental adhesive is a product including Bis-GMA, HEMA, solvents, water, acetone, optionally containing further nanofillers.

9. The process according to claim 8 wherein the further nanofillers are silicate.

10. Process according to claim 1, wherein said nanofiller suspension is obtained starting from graphene in powder.

11. The process according to claim 1, wherein the graphene nanoplatelets (GNP) are obtained from expanded graphite by liquid-phase exfoliation by sonication.

12. The process according to claim 11, wherein:
   step a comprises preparation of a suspension of expanded graphite in aqueous solution of ethanol at 99% having expanded graphite concentration between 0.1 mg/mL and 1 mg/mL, sonication with a power output per unit of surface transferred from the tip of the sonotrode to the liquid between 20% and 100% of the maximum value that the sonotrode can provide, with a pulsed cycle 1 sec on-phase and 1 second off-phase, for a total time of activity between 10 and 60 minutes, at a controlled temperature comprised between 10 and 20° C.;
   step b comprises addition of an amount polymer adhesive to the suspension of GNP in ethanol at 99% according to the following formula:

$V\_GNP\_suspension = 10 \times W\_GNP \% \times P\_polymer/C$

Wherein W_GNP (%) is the GNP weight in percent over the weight of polymer adhesive, and C is the concentration of expanded graphite in ethanol as specified in step a; and
   step b is followed by steps c, d, and e, as recited in claim 1.

13. The process according to claim 12 wherein the power output per unit of surface transferred from the tip of the sonotrode to the liquid is 70% of the maximum value that the sonotrode can provide.

14. The process according to claim 11 wherein sonication is carried out for 20 minutes at a temperature of 15° C.

15. The process according to claim 1, in wherein the solvent can be aqueous solution of ethanol, organic or inorganic solvent, acetone, glutaraldehyde and their mixture.

16. An antimicrobial dental adhesive obtainable by the process of claim 1, made of graphene, or graphene-based nanostructures, graphene nanoplatelets, or graphene oxide nanoplatelets, or reduced graphene oxide nanoplatelets, or multilayers graphene flakes, or a combination thereof, uniformly dispersed in the polymer adhesive and partially exposed over the adhesive free-surface with their sharp geometry.

17. The antimicrobial dental adhesive according to claim 16, wherein the graphene nanostructures are decorated with microrods or nanorods of metal oxide.

18. The antimicrobial dental adhesive according to claim 17, wherein said graphene nanostructures are decorated with microrods or nanorods of zinc oxide.

19. The antimicrobial dental adhesive according to claim 18, wherein said graphene nanostructures decorated with microrods or nanorods of zinc oxide have diameter comprised between 20 nm and 500 nm and length comprised between 200 nm and 3 μm.

20. The antimicrobial dental adhesive according to claim 16, wherein said graphene nanostructures have lateral dimensions comprised between 200 nm and 10 micron and thickness comprised between 1 nm and 100 nm.

21. The antimicrobial dental adhesive according to claim 16, wherein said graphene nanostructures have a weight concentration comprised between 0.05% wt and 0.5% wt.

22. The antimicrobial dental adhesive according to claim 16 having viscosity comprised between 0.01 and 0.1 Pa·s.

* * * * *